United States Patent [19]

Nesmeyanov et al.

[11] 3,950,373

[45] Apr. 13, 1976

[54] METHOD FOR ISOLATING ORGANOMETALLIC COMPOUNDS AND THIOUREA ADDUCTS WITH ORGANOMETALLIC COMPOUNDS

[76] Inventors: Alexandr Nikolaevich Nesmeyanov, glavnoe zdanie MGU, korpus K, kv. 105; Margarita Iosifovna Rybinskaya, ulitsa Novatorov, 40, korpus 5, kv. 80; Georgy Borisovich Shulpin, B. Filevskaya ulitsa, 19/18, korpus 1, kv. 185, all of Moscow, U.S.S.R.

[22] Filed: Aug. 30, 1974

[21] Appl. No.: 502,106

[52] U.S. Cl. ................ 260/429 CY; 260/429 AR; 260/438.5 R; 260/439 CY
[51] Int. Cl.² ........................................ C07F 11/00
[58] Field of Search. 260/429 CY, 429 AR, 438.5 R

[56] References Cited
UNITED STATES PATENTS

| | | | |
|---|---|---|---|
| 3,067,227 | 12/1962 | Axtell et al.................. | 260/439 CY |
| 3,122,577 | 2/1964 | Lindstrom et al............ | 260/439 CY |

OTHER PUBLICATIONS

Chem. Abstracts Vol. 77, 61277g (1972).
Chem. Abstracts Vol. 52, 4380b,c (1958).
Chem. Abstracts Vol. 59, 8273b,c (1963).
Chem. Abstracts Vol. 69, 10809j (1968).
Chem. Abstracts, Vol. 56, 1350b,c (1962).
Chem. Abstracts, Vol. 71, 105759y (1969).
Chem. Abstracts, Vol. 69, 54864c (1968).
Chem. Abstracts, Vol. 71, 123673V (1969).
Chem. Abstracts, Vol. 64, 4988h (1966).

*Primary Examiner*—Helen M. S. Sneed
*Attorney, Agent, or Firm*—Haseltine, Lake & Waters

[57] ABSTRACT

The method for isolating organometallic compounds that are cyclopentadienyl or benzene $\pi$-complexes of transition metals having the general formula

LML' where
L is a non-substituted cyclopentadienyl ring or a non-substituted benzene ring;
L' is a non-substituted cyclopentadienyl ring, a non-substituted benzene ring, or carbonyl groups;
M is a transition metal, from a mixture with other substances consists in preparing adducts of organometallic compounds with thiourea which does not form such adducts with said substances. According to the invention, said mixture is processed with thiourea in a medium of an organic solvent to prepare entirely novel substances, which are not heretofore known, namely, thiourea adducts with said organometallic compounds. Said adducts are then separated from the substances that do not form such thiourea adducts, and decomposed to isolate the organometallic compounds.

15 Claims, No Drawings

METHOD FOR ISOLATING ORGANOMETALLIC COMPOUNDS AND THIOUREA ADDUCTS WITH ORGANOMETALLIC COMPOUNDS

This invention relates to a method for isolating organometallic compounds belonging to the class of cyclopentadienyl or benzene π-complexes of transition metals from mixtures with other substances by preparing adducts of said organometallic compounds with thiourea that does not form such adducts with said substances, and more specifically the invention relates to entirely novel compounds, viz., thiourea adducts with said organometallic compounds.

The proposed method can be used for isolating organometallic compounds that are cyclopentadienyl or benzene π-complexes of transition metals from the reaction mixture, for purification of organometallic compounds, and also for recovering an unreacted organometallic compound from the reaction mixture.

Said organometallic compounds are used as antiknock compounds, as biologically potent substances, as polymer stabilizers, insecticides, dyes, as additives to fuels, lacquers, varnishes, paints, oils, rubbers, and also for preparing metallic coatings.

Thiourea adducts with said organometallic compounds can be used for conservation of organometallic compounds that are otherwise unstable while under storage.

Prior art methods are known for isolating organometallic compounds, including organometallic compounds that are cyclopentadienyl or benzene π-complexes of transition metals having the general formula LML', where L is a non-substituted cyclopentadienyl or a non-substituted benzene ring, L' is a non-substituted cyclopentadienyl ring, a non-substituted benzene ring, or carbonyl groups, and M is a transition metal. For example, methods are known for distillation with steam, vacuum sublimation, recrystallization, chromatography. A particular method is selected depending on the type of organometallic compound, on the conditions of the reaction by which it is produced, and also on the required purity of the product. The most suitable method of isolation of ferrocene is by steam distillation. This method, however, is time-consuming, requires much labor and energy, and moreover, fails to recover completely all ferrocene from the reaction mixture. Other methods also suffer from some disadvantages: vacuum distillation requires complicated equipment, chromatography requires great amounts of alumina and solvents, recrystallization proves in some cases ineffective to purify organometallic compounds.

The object of this invention is to provide a convenient and simple method of isolating organometallic compounds.

Another object of the invention is to provide a method that would be suitable for isolation of a wide range of organometallic compounds from the reaction mixture in their preparation.

Still another object of the invention is to provide a method that would ensure high purity of the organometallic compounds obtained.

According to said and other objects the essence of the invention resides in a method for isolating organometallic compounds, that are cyclopentadienyl or benzene π-complexes of transition metals having the general formula

LML' where
L is a non-substituted cyclopentadienyl ring, or a non-substituted benzene ring,
L' is a non-substituted cyclopentadienyl ring, a non-substituted benzene ring, or carbonyl groups, and
M is a transition metal,
from its mixture with substances that do not form adducts with thiourea, in which, according to the invention, said mixture is processed with thiourea in the presence of an organic solvent, an alkanol having from 1 to 3 carbon atoms, dialkylketone, or a mixture of said alkanol with dialkylketone, the obtained adducts of thiourea with said organometallic compounds are separated from the substances that do not form such adducts with thiourea, after which the adducts are decomposed to give organometallic compounds.

Said mixture is treated with thiourea in a medium which is a mixture of an alkanol having from 1 to 3 carbon atoms, or dialkylketone, with benzene, its alkyl derivatives, carbon tetrachloride, or petroleum ether.

Alkanols are used in the process as both the medium and the initiators of the reaction between the organometallic compounds and thiourea.

If an alkanol having from 1 to 3 carbon atoms is an initiator, it should be taken in the quantity of not more than 20 per cent of the thiourea weight, and the thiourea processing should be carried out in a medium of benzene or of its alkyl derivaties.

If the thiourea processing is carried out in a medium of an organic solvent, e.g. an alkanol having from 1 to 3 carbon atoms, dialkylketone, or a mixture of said alkanol or dialkylketone with benzene, its alkyl derivatives, carbon tetrachloride or petroleum ether, said thiourea processing should be carried out with evaporation of the organic solvent to obtain a residue which is a mixture of the organometallic compounds thiourea adducts and substances that do not form adducts with thiourea, after which said adducts are separated from the substances that do not form thiourea adducts by washing out said substances with benzene or petroleum ether.

If the thiourea processing is carried out in a medium of benzene or of its alkyl derivatives in the presence of an alkanol taken in the quantity not more than 20 per cent of the thiourea weight, the organometallic compounds thiourea adducts should be separated from the substances that do not form such thiourea adducts by filtering.

It is recommended that the thiourea adducts be decomposed with water at a temperature of 5°–100°C.

It is also possible to decompose the thiourea adducts by heating them in an organic solvent, such as benzene or petroleum ether, at temperatures from 60°C to the boiling point of the given particular solvent.

Moreover, it is possible to decompose the thiourea adducts by subliming organometallic compounds therefrom.

Chromatographic methods of separation can also be used in the proposed method of isolating organometallic compounds. In this case a mixture of organometallic compounds, and substances that do not form thiourea adducts, in the form of a solution in an alkanol having from 1 to 3 carbon atoms, can be processed with thiourea by passing said solution through a bed which is a mixture of thiourea with alumina or silica gel taken in the weight ratio of thiourea to alumina or silica gel from 1:3 to 3:1, with the result that adducts of organometallic compounds with thiourea are formed. Substances that do not form thiourea adducts are separated from the obtained thiourea adducts by washing them out with an alkanol having from 1 to 3 carbon atoms, and the separated adducts are decomposed with water at a temperature of 5°–100°C to liberate organometallic compounds which are then extracted with an organic solvent.

If the mixture containing organometallic compounds is in the form of a solution in benzene, then before the thiourea processing, the bed, which is a mixture of thiourea and alumina or silica gel, is wetted with an alkanol having from 1 to 3 carbon atoms, or with a saturated solution of thiourea in said alkanol, and the elution process is effected with an alkanol having from 1 to 3 carbon atoms, or with a saturated solution of thiourea in said alkanol.

Organometallic compounds are isolated, according to the invention, through an intermediate step in which entirely novel substances, that have not been known before, are prepared. These new substances are thiourea adducts with organometallic compounds which are cyclopentadienyl or benzene $\pi$-complexes of transition metals having the general formula

LML' where L is a non-substituted cyclopentadienyl ring or benzene ring L' is a non-substituted cyclopentadienyl ring, a non-substituted benzene ring or carbonyl groups, and M is a transition metal.

Examples of such organometallic compounds are all bis($\pi$-cyclopentadienyl) metals, such as ferrocene, ruthenocene, osmocene, nickelocene; cyclopentadienyl metal tricarbonyls such as cyclopentadienylmanganese tricarbonyl cyclopentadienyl rhenium tricarbonyls; benzenemetal tricarbonyl, such as benzene tricarbonylchromium, benzenemolybdenumtricarbonyl, benzenetungstentricarbonyl; bis($\pi$-benzene)metals, such as bis-benzenechromium. This list, however, does not cover all classes of $\pi$-complexes of transition metals with which thiourea can from adducts. Adducts can only be formed by compounds containing no substituents in the benzene or cyclopentadienyl rings.

Said adducts are obtained by the interaction between thiourea and, for example, such organometallic compounds as ferrocene

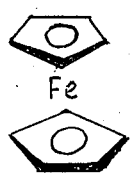

nickelocene

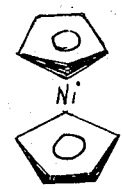

benzenetricarbonylchromium

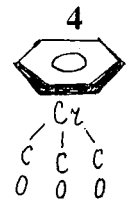

cyclopentadienyl tricarbonyl manganese

Thiourea adducts with said organometallic compounds are solid crystalline substances having the color of the organometallic compounds but with a paler tint.

The proposed method is simple to carry out, inexpensive, requires small quantities of reagents, solvents or energy.

An important advantage of the proposed method is that thiourea used in the process can be recovered and reused.

In some cases, for example in the isolation of ferrocene from a mixture with ethylferrocene, the proposed method is the only one that can be effective in separation of the mixture on an industrial scale.

Said method can be used in cases where it is necessary to improve the purity of organometallic compounds, the purity increasing with multiple repetition of the procedure.

The method of isolating organometallic compounds from a mixture with substances that do not form thiourea adducts can be carried out as follows.

A mixture of an organometallic compound with substances that do not form thiourea adducts is processed with thiourea. The adduct that is formed in the reaction between thiourea and the organometallic compound is separated from the substances that do not form such thiourea adducts. Finally, pure organometallic compound is isolated from the adduct.

The mixture of the organometallic compound with substances that do not form thiourea adducts is formed as a result of the reaction in which the given organometallic compound is produced.

Substances that do not form thiourea adducts are in this case the starting organic substances that are used in the reaction and also the products of resin formation. The adducts are separated from these admixtures by washing the organic solvents in which the thiourea adducts are only sparingly soluble.

If the organometallic compound does not react fully, the reaction mixture, in addition to the starting organometallic compound, the organic substances and resins, will also contain organometallic compounds substituted in the cyclopentadienyl or benzene ring with alkyl, aryl, aralkyl, functional groups, the halogens.

All organometallic ring-substituted compounds do not form thiourea adducts. Therefore, as soon as the thiourea adduct with the non-substituted organometallic compound is formed, the substituted compounds are washed from the adduct with an organic solvent in which the thiourea adduct is only sparingly soluble.

The proposed method, therefore, makes it possible to recover the starting organometallic compound from a mixture with its derivatives.

The interaction between organometallic compounds and thiourea is effected as follows.

A mixture of organometallic compound with substances that do not form thiourea adducts is used in the form of a solution in an organic solvent, such as methyl alcohol, ethyl alcohol, propyl alcohol, acetone, methylethyl-ketone, benzene, toluene, xylene, carbon tetrachloride, petroleum ether.

Said solution is processed with thiourea, which can be used both as a solid substance (crushed) and as a solution in methyl alcohol, ethyl alcohol, propyl alcohol, acetone or methyl ethylketone.

Solutions of any concentrations can be used, but saturated solutions are preferred. Solid thiourea is first moistened with an alkanol taken in an amount not exceeding 20 per cent of the weight of thiourea.

Organic solvents used in the process can be either anhydrous or can contain moisture.

The quantity of thiourea used to form adducts varies within the range from 2 to 15 mole per mole of organometallic compound.

The solution containing an organometallic compound, substances that do not form thiourea adducts, and thiourea, is heated in vacuum, or at atmospheric pressure, to remove the solvent. The residue on evaporation is a mixture of the thiourea adduct and substances that do not form such adducts with thiourea. The residue is washed with an organic solvent in which the adducts are only sparingly soluble, for example, with benzene or petroleum ether. These solvents remove substances that do not form thiourea adducts.

During crystallization, thiourea readily forms crystals with the framework in the form of channels, into which various substances can penetrate and fill them completely to form inclusion compounds, i.e., the adducts.

If the solution of a mixture containing organometallic compounds in benzene is processed with thiourea solution in an alkanol or diethyl ketone, the adduct of thiourea with the organometallic compound precipitates either on evaporation of the solvent, or on cooling. Substances that do not form adducts remain in solution. The temperature of the solution in this case varies from room temperature to the temperature at which the solvent boils. The thiourea adducts are separated by filtration or decantation.

The adducts are formed also in a medium of benzene by the interaction between the organometallic compound and solid (finely crushed) thiourea wetted, for example), with methyl alcohol, taken in an amount not exceeding 20 per cent of the weight of thiourea, the alcohol in this case performing the role of the initiating agent. The organometallic compound gives a solid crystalline adduct which is then separated by filtration or decantation from substances that do not form such adducts.

Thiourea adducts with organometallic compounds are solid crystalline substances, mostly stable in storage at room temperature. If the adduct is heated, the organometallic compound is isolated therefrom. For example, when heated to a temperature from 70° to 100°C in petroleum ether (b.p. 100°–120°C), a suspension of a thiourea adduct with ferrocene liberates ferrocene which passes into solution.

Thiourea adducts with organometallic compounds can be separated by various methods from substances that do not form such adducts.

If a mixture, containing an organometallic compound, is taken in the form of its solution in an organic solvent in which the adduct is only poorly soluble, for example in benzene, and is acted upon by a solution of thiourea in alkanol or dialkyl ketone, or by solid (crushed) thiourea, the separation of the precipitated adduct is effected by filtration, decantation, or centrifuging. The temperature of the solution should be in this case 20°C or below room temperature.

If after evaporation of the organic solvent the residue contains the adduct and substances that do not form such adducts, the residue is washed with an organic solvent in which the adducts are poorly soluble, while the substances that do not form the adducts are readily soluble in it, for example, petroleum ether or benzene.

After separation, the solid crystalline adduct is washed to remove admixtures, and dried at a temperature below its decomposition point. The adducts are washed with an organic solvent, in which the adducts are poorly soluble, at a temperature below their decomposition point.

The obtained adducts are decomposed by various methods. The preferable method is by treating the adducts with water at a temperature of 5°–100°C, preferably at 50°–100°C. Thiourea is dissolved in water to liberate the pure organometallic compound.

Thiourea can be recovered from the aqueous solution and reused in the process. The organometallic compound is extracted with benzene or petroleum ether, or separated by passing through a filter, after which it is washed with water and dried at a temperature below its decomposition point.

Moreover, the adduct can be decomposed by heating in benzene or petroleum ether at temperatures above its decomposition point.

The adducts can also be decomposed by subliming organometallic compounds therefrom in a vacuum of 2–80 mm Hg, or at atmospheric pressure.

The chromatographic principle of separation can also be used in the proposed method of isolating organometallic compounds. In this case, the mixture of organometallic compounds and substances that do not form thiourea adducts is processed with thiourea by passing this mixture through a bed which is a mixture of thiourea and an adsorbing material such as alumina or silica gel. The weight ratio of thiourea to said adsorbing material can vary from 1:3 to 3:1.

The mixture containing the organometallic compound can be in the form of a solution in benzene or an alkanol, e.g., in methyl or ethyl alcohol. If benzene is used as a solvent, the mixture of thiourea and alumina or silica gel is wetted with an alkanol, for example, ethyl alcohol, methyl alcohol, or an unsaturated solution of thiourea in said alkanols.

A mixture of thiourea with aluminum oxide or silica gel can be used in the form of a column or a plate upon which the solution of the mixture containing the organometallic compound is applied, as a result of which thiourea forms an adduct with the organometallic compound.

Substances that do not form adducts with thiourea are separated from the obtained adducts by elution with alkanols, for example, with methyl alcohol, or with a saturated solution of thiourea is an alkanol.

In order to decompose thiourea adducts, the mixture of alumina or silica gel with the adducts is treated with water at a temperature of 5°–100°C, and then the organometallic compound is extracted with an organic solvent in which thiourea is poorly soluble, for example with benzene.

For a better understanding of the invention, the following examples of its practical embodiment are given by way of illustration.

EXAMPLE 1

Isolation of ferrocene from the reaction mixture which is formed in its preparation.

The reaction of preparing ferrocene is carried out as follows.

A reaction flask provided with a stirrer, a reflux condenser, a dropping funnel, and an argon delivery tube, is charged with 6 ml of anhydrous diethylamine and cooled to 10°C. Then, within 15 minutes, 6.0 g of anhydrous ferric chloride are added to the flask. Next, within 30 minutes, a mixture of 6.5 ml (freshly distilled) monomer of cyclopentadiene and 6.0 ml of anhydrous diethylamine cooled to −10°C is added to the reaction mixture, which is stirred for four hours at a temperature of 20°C and then allowed to stand overnight.

100 ml of acetone are added to the reaction mixture, the suspension obtained is filtered, the precipitate is washed with acetone, and the acetone extracts are combined with the main solution. Then 200 ml of a solution containing 20 g of thiourea in acetone are added at 60°C to the solution containing the ferrocene obtained in the reaction. The solvent is evaporated in a vacuum of 20 mm Hg at a temperature of 25°C. The residue containing the adducts of thiourea with ferrocene and side products of the reaction are transferred onto a filter, dried in air at a temperature of 25°C and washed with 100 ml of benzene. The obtained residue is dried in air, processed with 200 ml of boiling water, and dried at a temperature of 40°C. Then it is washed with petroleum ether (b.p. 40°–70°C) at a temperature of 10°C. The yield of ferrocene is 3 g. M.p. 173°C.

EXAMPLE 2

9.3 g of technical ferrocene prepared by steam distillation from the reaction mixture obtained as described in Example 1, are purified by dissolving in 100 ml of benzene and adding a solution of 1.9 g of thiourea in 50 ml of methanol. The precipitated yellow needles are separated on a filter, washed with benzene at a temperature of 20°C, and dried at a temperature of 20°C. The result is 0.6 g of dry thiourea adduct with ferrocene. The obtained adduct corresponds (approximately) to the composition of $C_{10}H_{10}Fe.3.5CH_4N_2S$.

Calculated, %: C, 35.83; H, 5.35; N, 21,67; S, 24.80; Fe, 12.34. Found, %: C, 36.81; H, 5.36, N, 22.05; S, 24.79; Fe, 9.29; C, 36.86; H, 5.48; N, 22.08; S, 24.90; Fe, 9.41.

The infra-red absorption spectrum of the obtained adduct thiourea ferroene adduct thus obtained exhibits two strong bands at $\nu = 1010$ cm$^{-1}$ and $\nu = 1111$ cm$^{-1}$, which are due to oscillations of non-substituted cyclopentadienyl rings of ferrocene. The whole infra-red spectrum of the adduct is actually composed of superimposed ferrocene and thiourea spectra.

The obtained product is decomposed with water as in Example 1 to prepare pure ferrocene having a melting point of 173°C.

EXAMPLE 3

To purify technical ferrocene, 0.5 g is dissolved in 20 ml of acetone, the solution is heated to 60°C and a solution of 4.0 g of thiourea in 60 ml of methyl alcohol, also heated to 60°C, is added to it. The solvent is then evaporated by boiling for 60 minutes, the residue is washed with petroleum ether (b.p. 40°–70°C) at a temperature of 20°C and dried at a temperature of 40°C. Ferrocene is isolated from the adduct by sublimation at a temperaure of 200°–250°C. The obtained pure ferrocene has a melting point of 173°C.

EXAMPLE 4

A mixture of 0.5 g of ferrocene and 0.5 g of 1,1-diethylferrocene is dissolved in 50 ml of carbon tetrachloride, the solution is heated to a temperature of 80°C and a solution of 7.0 g of thiourea in 200 ml of 96 per cent ethyl alcohol is added to it.

The solvent is then evaporated in a vacuum of 20 mm Hg at a temperaure of 40°C.

The obtained residue is a mixture of the thiourea adduct with ferrocene and 1,1'-diethylferrocene. It is washed with benzene until the extracts are colorless.

The benzene solution is evaporated to prepare 0.4 g of 1,1'-diethylferrocene containing ferrocene as admixture.

The adduct is decomposed by adding petroleum ether (b.p. 100°–120°C) thereto and heating the obtained suspension to a temperature of 70°–100°C. After evaporation of the solvent, pure ferrocene is obtained. Its melting point is 173°C.

EXAMPLE 5

0.8 g of a mixture of cyanoferrocene and ferrocene, prepared by cyanation of ferrocene, is dissolved in 125 ml of petroleum ether (b.p. 40°–70°C); the obtained solution, at a temperature of 40°C, is added to a solution of thiourea in methyl alcohol. The solvent is evaporated to dryness in a vacuum of 20 mm Hg at a temperature of 30°C. The obtained residue is washed with benzene at a temperature of 20°C and decomposed with water as described in Example 1 to give ferrocene. The benzene layer is evaporated to dryness, the residue is dissolved in 25 ml of acetone, and 5.0 g of thiourea in 50 ml of methyl alcohol are added at a temperature of 60°C. The solvent is then evaporated in vacuum at 30°C, the residue is washed with benzene until the extract is colorless; the benzene solution is washed with water, and benzene is finally removed by evaporation. The obtained cyanoferrocene is recrystallized from hexane (m.p. 107°C). In order to ensure better purification of cyanoferrocene from ferrocene, the procedure is repeated.

EXAMPLE 6

A mixture of 0.9 g of ferrocene and 0.1 g of 1,1'-diacetylferrocene is dissolved in 30 ml of benzene, and a solution of 10 g of thiourea in 10 ml of methyl alcohol, at a the temperature of 60°C, is added to the solution. The solvent is evaporated in a vacuum of 20 mm Hg at a temperature of 30°C, and the residue is washed with benzene until the extract is colorless, after which the residue is dried at a temperature of 30°C.

0.05 g of 1,1' diacetylferrocene containing ferrocene admixture is obtained from the benzene solution.

The adducts are decomposed with water at a temperature of 80°C. Crystals of ferrocene are separated by filtration, and the yield is 0.8 g of ferrocene having a melting point of 173°C. Thiourea can be recovered from the aqueous solution and reused in the process.

EXAMPLE 7

A mixture of 0.5 ferrocene and 0.1 g of 1,1'-diacetylferrocene is dissolved in 25 ml of benzene, and the obtained solution is shaken for 15 hours with 3 g of solid thiourea moistened with 0.5 ml of methyl alcohol (about 15 per cent of the weight of thiourea).

The result of the reaction is a solid adduct of thiourea with ferrocene, which is decomposed by a procedure described in Example 1 to prepare 0.3 g of ferrocene having a melting point of 173°C. 1,1'-diacetylferrocene containing admixtures of ferrocene is isolated from the benzene solution.

EXAMPLE 8

A mixture of ferrocene and cyanoethylated ferrocenes [$\beta$-cyanoethylferrocene, 1,1'-, 1,2- and 1,3-bis($\beta$-cyanoethyl)ferrocenes] prepared in the cyanoethylation of ferrocene, containing 18.6 g of ferrocene, 45 ml of $\beta$-chloropropionitrile and 50 g of aluminum chloride, followed by oxidation with quinone and reduction with tin chloride, is dissolved in 200 ml of benzene. To this solution are added 200 ml of a saturated solution of thiourea in methyl alcohol. The solvent is evaporated in a vacuum of 15 mm Hg to a volume of 100 ml, and cooled to 10°C.

The precipitated yellow substance is the adduct of thiourea with ferrocene which is decanted and washed with benzene.

The benzene extracts are combined with the mother liquor obtained in decantation, and washed with water at a temperature of 40°C.

Benzene is evaporated in a vacuum of 20 mm Hg at a temperature of 40°C.

The obtained residue is separated into cyanoethylated ferrocenes on a column packed with aluminum oxide.

The thiourea adduct with ferrocene is decomposed as in Example 1, and ferrocene that did not participate in the cyanoethylation reaction, is isolated.

EXAMPLE 9

To purify nickelocene from resinous products that are formed in the reaction by which it is prepared, 0.1 of this substance is dissolved in 5 ml of benzene, and at a temperature of 20°C, 5 ml of a saturated solution of thiourea in methyl alcohol are added.

The precipitated adduct of thiourea with nickelocene is separated on a filter and washed with benzene at a temperature of 20°C until the extracts are colorless. The obtained product is 0.12 g of the adduct in the form of pale green needles.

The adduct is decomposed with water at a temperature of 5°C. Pure nickelocene is extracted with petroleum ether to prepare 0.06 g of nickelocene having a melting point of 173°C (with decomposition).

EXAMPLE 10

To purify benzene chromium tricarbonyl from side products formed in the reaction by which it is produced, 0.02 g is dissolved in 3 ml of benzene, and 2 ml of a saturated solution of thiourea in methyl alcohol are added at a temperature of 20°C.

The solvent is evaporated and the residue is washed with benzene to prepare the adduct of thiourea with benzene chromium tricarbonyl in the form of pale yellow needles which are decomposed with water at a temperature of 15°C. Pure benzene chromium tricarbonyl is extracted with benzene. The melting point of the pure product is 165°C.

EXAMPLE 11

To purify technical cyclopentadienylmanganese tricarbonyl having a melting point at 69°–72°C, 0.5 g of the said substance is dissolved in 50 ml of methyl alcohol, and 4.0 g of thiourea are added to the obtained solution. The solvent is evaporated in a vacuum of 20 mm Hg at a temperature of 30°C.

The obtained residue is washed with petroleum ether (b.p. 40°–70°C) at a temperature of 20°C until the extracts are colorless, and dried at a temperature of 20°C. The resultant product comprises 4.2 g of the thiourea adduct with cyclopentadienylmanganese tricarbonyl in the form of a yellowish crystalline powder.

The infra-red spectrum of this adduct exhibits two bands at $\nu = 1932$ cm$^{-1}$ and $\nu = 2015$ cm$^{-1}$ which are characteristic of the oscillations of the carbonyl groups of cyclopentadienylmanganese tricarbonyl. Said spectrum is a superimposition of the spectra of cyclopentadienylmanganese tricarbonyl and thiourea.

The adduct is decomposed with water at a temperature of 20°C. Cyclopentadienylmanganese tricarbonyl is extracted with 200 ml of petroleum ether, the obtained solution is dried over sodium sulfate, evaporated to a volume of 5 ml, and cooled to 0°C.

The precipitated crystals are separated on a filter and dried at a temperature of 20°C in a vacuum of 20 mm Hg. The resultant product is 0.4 g of cyclopentadienylmanganese tricarbonyl having a melting point of 77°C.

EXAMPLE 12

To purify technical cyclopentadienylmanganese tricarbonyl, having a melting point at 69°–72°C, from admixtures, one gram is dissolved in 10 ml of toluene, and 3.5 g of thiourea in 150 ml of anhydrous ethyl alcohol at a temperature of 55°C, are added to the obtained solution.

The solvent is evaporated in a vacuum of 20 mm Hg at a temperature of 30°C, the residue is washed with benzene at a temperature of 20°C until the extracts are colorless, and dried in air.

The resultant product comprises 2.9 g of thiourea adduct with cyclopentadienyl manganese tricarbonyl in the form of a yellowish powder.

To decompose the adduct, it is placed in a separatory funnel, and 100 ml of water at a temperature of 45°C and 30 ml of benzene are poured into it. After shaking, the benzene solution is dried over sodium sulphate, and benzene is evaporated.

The yield of pure cyclopentadienylmanganese tricarbonyl having the melting point at 77°C, is 0.3 g.

EXAMPLE 13

A mixture of 0.5 g of cyclopentadienylmanganese tricarbonyl, 0.1 g of acetylcyclopentadienylmanganese tricarbonyl, and 3.5 g of thiourea, is dissolved in 100 ml of anhydrous ethyl alcohol. The alcohol is evaporated by boiling, and the residue, which is a mixture of thiourea adduct with cyclopentadienylmanganese tricarbonyl and acetylcyclopentadienylmanganese tricarbonyl is washed with 100 ml of petroleum ether (b.p. 40° – 70°C). This extract contains acetylcyclopentadienylmanganese tricarbonyl.

The adduct is decomposed as in Example 10, and cyclopentadienylmanganese tricarbonyl is isolated.

EXAMPLE 14

A mixture of ferrocene and 1,1'-diethylferrocene (1:1) in the form of its saturated solution in benzene is applied in the amount of 3 ml to a column of a mixture of thiourea and aluminum oxide (the weight ratio of thiourea to aluminum oxide 1:1), wetted with methyl alcohol taken in the amount of 20 per cent of the weight of the thiourea.

1,1'-Diethylferrocene is eluted with methylalcohol.

In order to decompose the adduct, the mixture of alumina and the adduct of thiourea with ferrocene is processed with water at a temperature of 30°C. Ferrocene is extracted from the obtained suspension with benzene.

EXAMPLE 15

The column is filled with a mixture of thiourea and aluminum oxide (the weight ratio of thiourea to alumina 1:3) moistened with a saturated solution of thiourea in methyl alcohol taken in the amount of 18 per cent of the weight of thiourea present in the column in the mixture with aluoxide. Then, a solution of 0.2 g of a mixture of ferrocene and 1,1'-diethylferrocene in 3 ml of benzene is applied to the column. 1,1'-diethylferrocene is eluted with a saturated solution of thiourea in methyl alcohol.

The adduct is decomposed as in Example 14.

EXAMPLE 16

A solution of a mixture of ferrocene and acetylferrocene in methyl alcohol is applied to a plate with a thin layer of a finely ground mixture of thiourea and silica gel (the weight ratio of thiourea to silica gel of 1:1), and acetylferrocene is washed out with methyl alcohol.

Acetylferrocene moves together with the solvent front while the adducts of thiourea with ferrocene move slower.

To decompose the adducts, the strips containing these adducts are processed with boiling water and ferrocene is extracted from the obtained suspension with benzene.

EXAMPLE 17

A solution of a mixture of cyclopentadienyl manganese tricarbonyl and acetylcyclopentadienyl manganese tricarbonyl in methyl alcohol is applied to a plate with a thin layer of a finely ground mixture of thiourea and aluminum oxide (the weight ratio of thiourea to aluminum oxide of 3:1) and acetylcyclopentadienyl-manganese tricarbonyl is eluted with ethyl alcohol. The substance moves together with the solvent front, while the thiourea adducts with cyclopentadienylmanganese tricarbonyl move slower.

The adducts are decomposed and cyclopentadienyl-manganese tricarbonyl is isolated as described in Example 16.

We claim:

1. Thiourea adduct with ferrocene.
2. Thiourea adduct with nickelocene.
3. Thiourea adduct with benzene chromium tricarbonyl.
4. Thiourea adduct with cyclopentadienylmanganese tricarbonyl.
5. A method for isolating an organometallic compound selected from the group consisting of ferrocene, ruthenocene, osmocene, nickelocene, cyclopentadienyl manganese tricarbonyl, cyclopentadienyl rhenium tricarbonyl, benzene chromium tricarbonyl benzene molybdenum tricarbonyl, benzene tungsten tricarbonyl and bis-benzene chromium from a mixture with substances that do not form adducts with thiourea comprising treating said mixture with thiourea in the presence of an organic solvent selected from the group consisting of alkanols having from 1 to 3 carbon atoms, dialkyl ketones and mixtures of said alkanols and said ketones to form a thiourea adduct of said organometallic compound; separating said thiourea adduct from the substances that do not form thiourea adducts; and decomposing said thiourea adduct to isolate said organometallic compound.
6. A method according to claim 5, in which the treatment with thiourea is carried out in a mixture of said solvent with a second organic solvent selected from the group consisting of benzene, alkyl derivatives of benzene, carbon tetrachloride and petroleum ether.
7. A method according to claim 5, in which said alkanol is taken in an amount not exceeding 20 per cent of the weight of the thiourea and in admixture with a second organic solvent selected from the group consisting of benzene and its alkyl derivatives.
8. A method according to claim 5, in which the thiourea treatment is carried out with evaporation of the organic solvent to prepare a residue which is a mixture of the thiourea adduct with the organometallic compound and of said substances that do not form thiourea adducts, followed by separating said adduct from said substances that do not form thiourea adducts by washing said substances out with benzene or petroleum ether.
9. A method according to claim 6, in which the thiourea treatment is carried out with evaporation of the organic solvent to prepare a residue which is a mixture of the thiourea adduct with the organometallic compound and of said substances that do not form thiourea adducts, followed by separating said adduct from said substances that do not form thiourea adducts by washing said substances out with benzene or petroleum ether.
10. A method according to claim 7, in which the thiourea adduct of said organometallic compound is separated by filtration from said substances that do not form thiourea adducts.
11. A method according to claim 5, in which the thiourea adduct is decomposed by water at a temperature of 5°–100°C.
12. A method according to claim 5, in which the thiourea adduct is decomposed by heating in an organic solvent selected from the group consisting of benzene and petroleum ether at a temperature from 60°C up to the temperature at which said solvent boils.
13. A method according to claim 5, in which the thiourea adduct is decomposed by subliming said organometallic compound from said adduct.
14. A method for isolating an organometallic compound selected from the group consisting of ferrocene, ruthenocene, osmocene, nickelocene, cyclopentadienyl manganese tricarbonyl, cyclopentadienyl rhenium tricarbonyl, benzene chromium tricarbonyl, benzene molybdenum tricarbonyl, benzene tungsten tricarbonyl and bis-benzene chromium from a mixture with substances that to not form adducts with thiourea comprising passing a solution of said mixture in an alkanol having 1 to 3 carbon atoms through a bed consisting of a mixture of thiourea and an adsorbent selected from the group consisting of alumina and silica gel in a weight ratio of thiourea to said adsorbent of from 1:3 to 3:1 to form an adduct of thiourea with said organometallic compound, washing said bed with an alkanol having 1 to 3 carbon atoms to remove the substances which do not form adducts with thiourea, decomposing said adduct of thiourea and the organometallic compound with water at a temperature of 5°–100°C. to liberate the organometallic compound and extracting said organometallic compound with an organic solvent.

15. A method for isolating an organometallic compound selected from the group consisting of ferrocene, ruthenocene, osmocene, nickelocene, cyclopentadienyl manganese tricarbonyl, cyclopentadienyl rhenium tricarbonyl, benzene chromium tricarbonyl, benzene molybdenum tricarbonyl, benzene tungsten tricarbonyl and bis-benzene chromium from a mixture with substances that do not form adducts with thiourea comprising passing a soluton of said mixture in benzene through a bed consisting of a mixture of thiourea and an adsorbent selected from the group consisting of alumina and silica gel in a weight ratio of thiourea to said adsorbent of from 1:3 to 3:1, said bed being moistened with a saturated solution of thiourea in an alkanol having from 1 to 3 carbon atoms, to form an adduct of thiourea and said organometallic compound, washing said bed with a saturated solution of thiourea in an alkanol having from 1 to 3 carbon atoms to wash out from said bed the substances which do not form adducts with thiourea, decomposing said adduct with water at a temperature of 5°–100°C. to liberate the organometallic compound and then extracting the organometallic compound with an organic solvent.

* * * * *